United States Patent [19]
Urbahns et al.

[11] Patent Number: 5,670,525
[45] Date of Patent: Sep. 23, 1997

[54] SUBSTITUTED 4-PHENYL-6-AMINO-NICOTINIC ACID COMPOUNDS USEFUL IN THE TREATMENT OF CNS DISORDERS

[75] Inventors: Klaus Urbahns; Siegfried Goldmann, both of Wuppertal; Hans-Georg Heine, Krefeld; Bodo Junge; Rudolf Schohe-Loop, both of Wuppertal; Henning Sommermeyer, Köln; Thomas Glaser, Overath; Reilinde Wittka, Köln; Jean-Marie Viktor De Vry, Rösrath, all of Germany

[73] Assignee: Bayer Aktiengesellschaft, Leverkusen, Germany

[21] Appl. No.: 517,873

[22] Filed: Aug. 22, 1995

[30] Foreign Application Priority Data

Aug. 29, 1994 [DE] Germany .................. 44 30 638.5

[51] Int. Cl.⁶ .................. C07D 213/80; C07D 213/803; A61K 31/435; A61K 31/455
[52] U.S. Cl. .................. 514/334; 514/344; 514/352; 546/257; 546/289; 546/307
[58] Field of Search .................. 546/257, 289, 546/308, 307; 514/334, 344, 353, 352

[56] References Cited

PUBLICATIONS

S.E. Zayed, et al., Collect. Czech. Chem. Commun., vol. 56, pp. 2175–2182, (1991).
A.A. Krauze, et al., English version of Khimiya Geterotsiklicheskikh Soedinenii, No. 11, pp. 1504–1508, (1984).
P.W.L. Tas, et al., Neuroscience Letters, vol. 94, pp. 279–284, (1988).

R. Troschütz, et al., Arch. Pharm. (Weinheim), vol. 324, pp. 73–77, (1991).

M.M. Marugán, et al., Liebigs Ann. Chem., No. 2, pp. 145–149, (1989).

J.C. Ellory, et al., Br. J. Pharmacol., vol. 111, pp. 903–905, (1994).

J.C. Ellory, et al., Br. J. Pharmacol., vol. 106, pp. 972–977, (1992).

J.C. Ellory, et al., FEBS, vol. 296, No. 2, pp. 219–221, (1992).

Chemical Abstracts, vol. 102, abstract No. 78686x, p. 581, (1985).

Primary Examiner—Zinna Northington Davis
Attorney, Agent, or Firm—Sprung Horn Kramer & Woods

[57] ABSTRACT

The application relates to substituted 4-phenyl-6-amino-nicotinic acid derivatives for therapeutic use, to novel active compounds and to their use as cerebrally active agents. The active compounds are prepared by oxidizing appropriately substituted dihydropyridines according to customary methods.

13 Claims, No Drawings

SUBSTITUTED 4-PHENYL-6-AMINO-NICOTINIC ACID COMPOUNDS USEFUL IN THE TREATMENT OF CNS DISORDERS

The present invention relates to substituted 4-phenyl-6-amino-nicotinic acid derivatives, which are known in some cases, as medicaments, novel active compounds, a process for their preparation, and their use as potassium channel modulators, in particular for the treatment of the central nervous system.

A few 4-phenyl-3-pyridinecarboxylic acid derivatives are known from the publications Collect. Czech. Chem. Comun. 56 (10), 2175–82, 1991 and Khim. Geterotsikl. Soedin., (11), 1504–8, 1984, but no pharmacological action is described.

It has now been found that the substituted 4-phenyl-6-amino-nicotinic acid derivatives, which are known in some cases, of the general formula (I)

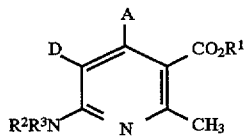

(I)

in which

A represents aryl having 6 to 10 carbon atoms or pyridyl, each of which is optionally substituted up to 3 times by identical or different substituents from the group consisting of nitro, cyano, phenyl, halogen and trifluoromethyl or by straight-chain or branched alkylthio or alkoxy in each case having up to 6 carbon atoms, D represents cyano or nitro, $R^1$ represents hydrogen or straight-chain or branched alkyl having up to 8 carbon atoms, $R^2$ and $R^3$ are identical or different and represent hydrogen or straight-chain or branched alkyl or acyl in each case having up to 6 carbon atoms and their salts surprisingly have a modulating action on potassium channels and are thus suitable for use in the control of cerebral disorders and sickle cell anemia.

In the context of the invention, physiologically tolerable salts are preferred. Physiologically tolerable salts are in general salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonic acid.

The compounds according to the invention can exist in stereoisomeric forms which either behave as image and mirror image (enantiomers) or which do not behave as image and mirror image (diastereomers). The invention relates both to the antipodes and to the racemic forms as well as to the diastereomer mixtures. Like the diastereomers, the racemic forms can also be separated into the stereoisomerically uniform constituents in a known manner.

Preferred compounds of the general formula (I) are those in which

A represents phenyl or naphthyl, each of which is optionally substituted up to 3 times by identical or different substituents from the group consisting of nitro, cyano, fluorine, chlorine, bromine, iodine, phenyl and trifluoromethyl or by straight-chain or branched alkylthio or alkoxy in each case having up to 4 carbon atoms, D represents cyano or nitro, $R^1$ represents hydrogen or straight-chain or branched alkyl having up to 6 carbon atoms, $R^2$ and $R^3$ are identical or different and represent hydrogen or straight-chain or branched alkyl or acyl in each case having up to 4 carbon atoms, and their salts, in the control of cerebral disorders.

Particularly preferred compounds of the general formula (I) are those in which

A represents phenyl which is optionally substituted up to 2 times by identical or different substituents from the group consisting of nitro, cyano, fluorine, chlorine, bromine, iodine, phenyl, trifluoromethyl, methoxy and methylthio, D represents cyano or nitro, $R^1$ represents hydrogen or straight-chain or branched alkyl having up to 4 carbon atoms, $R^2$ and $R^3$ are identical or different and represent hydrogen or straight-chain or branched alkyl or acyl in each case having up to 3 carbon atoms, and their salts, in the control of cerebral disorders.

The compounds of the general formula (I) according to the invention show an unforeseeable, useful spectrum of pharmacological action.

They are channel modulators having selectivity for calcium-dependent potassium. channels of high conductivity (BK(Ca) channels), in particular of the central nervous system.

On account of these pharmacological properties, they are suitable for the production of medicaments for the treatment of degenerative central nervous system disorders, such as e.g. on occurrence of dementias: multiinfarct dementia (MID), primary degenerative dementia (PDD), presenile and senile Alzheimer's disease, HIV dementia and other forms of dementia, additionally for the treatment of Parkinson's disease or amyotropic lateral sclerosis and also multiple sclerosis.

The active compounds are furthermore suitable for the treatment of brain function disorders in old age, of organic brain syndrome (OBS) and of age-related memory disorders (age-associated memory impairment, AAMI).

They are suitable for the prophylaxis, treatment and control of the sequelae of cerebral circulatory disorders such as cerebral ischaemias, strokes, craniocerebral traumata and subarachnoid haemorrhages.

They are useful for the treatment of depressions and psychoses, e.g. schizophrenia. They are additionally suitable for the treatment of disorders of neuroendocrine secretion and of neurotransmitter secretion and health disorders connected therewith such as mania, alcoholism, drug abuse, dependence or abnormal eating behaviour. Other application areas are the treatment of migraine, sleep disorders and of neuropathies. They are moreover suitable as analgesics.

The active compounds are furthermore suitable for the treatment of disorders of the immune system, in particular of T-lymphocyte proliferation and for affecting the smooth musculature, in particular of uterus, urinary bladder and bronchial tract and for the treatment of diseases connected therewith such as e.g. asthma and urinary incontinence or for the treatment of high blood pressure, arrhythmia, angina and diabetes.

The invention also relates to novel substances of the general formula (I) in which A, D, $R^1$ to $R^3$ have the meaning specified, but where the following compounds are excluded:

ethyl 6-amino-5-cyano-2-methyl-4-phenyl-nicotinoate ethyl 6-amino-4-(4-chlorophenyl)-5-cyano-2-methyl-nicotinoate ethyl 6-amino-5-cyano-2-methyl-4-(4-methoxyphenyl)-nicotinoate ethyl 6-amino-5-cyano-2-methyl-4-(4-nitrophenyl)-nicotinoate.

The invention preferably relates to the novel compounds of the general formula (Ia)

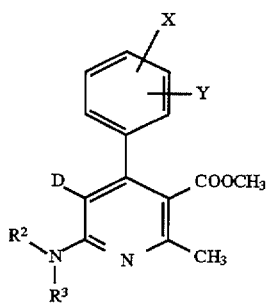

and their salts, having the substituent meanings specified in the following table:

| X, Y | $R^2$ | $R^3$ | D |
|---|---|---|---|
| 4-CF$_3$, H | H | H | NO$_2$ |
| 2-Cl, 3-Cl | H | H | NO$_2$ |
| H, H | H | H | NO$_2$ |
| 3-Cl, 4-CF$_3$ | H | H | NO$_2$ |
| 3-NO$_2$, H | H | H | NO$_2$ |
| 2-CF$_3$, H | H | H | NO$_2$ |
| 3-Cl, H | H | H | NO$_2$ |
| 2-Cl, 3-Cl | H | H | NO$_2$ |
| 2-Cl, 3-Cl | H | H | NO$_2$ |
| 4-OCH$_3$, H | H | H | NO$_2$ |
| 4-CN, H | H | H | NO$_2$ |
| 3-Cl, H | H | H | NO$_2$ |
| 2-CF$_3$, 3-H | CO—CH$_3$ | CO—CH$_3$ | NO$_2$ |
| 2-Cl, 3-Cl | CH$_3$ | H | NO$_2$ |
| H, H | CH$_3$ | H | NO$_2$ |
| 3-Cl, 4-CF$_3$ | CH$_3$ | H | NO$_2$ |
| 4-CF$_3$, H | CH$_3$ | H | NO$_2$ |
| 3-NO$_2$, H | CH$_3$ | H | NO$_2$ |
| 2-CF$_3$, H | CH$_3$ | H | NO$_2$ |
| 2-Cl, 3-Cl | CH$_3$ | H | NO$_2$ |
| H, H | —CO—CH$_3$ | H | NO$_2$ |
| 2-CF$_3$, 3-H | —CO—CH$_3$ | H | NO$_2$ |
| 2-Cl, 3-Cl | H | H | CN |
| 3-NO$_2$, H | H | H | CN |
| H, H | H | H | CN |
| 2-CF$_3$, H | H | H | CN |
| 4-Cl, H | H | H | CN |
| 2-CH$_3$, H | H | H | CN |
| 4-C$_6$H$_5$, H | H | H | CN |
| 2-Cl, 3-Cl | —COCH$_3$ | H | CN |
| 3-NO$_2$, H | —COCH$_3$ | H | CN |
| 2-CF$_3$, H | —COCH$_3$ | H | CN |
| 4-CF$_3$, H | —COCH$_3$ | H | CN |
| 2-Cl, 3-Cl | CH$_3$ | H | CN |
| 3-NO$_2$, H | CH$_3$ | H | CN |
| 2-CF$_3$, H | CH$_3$ | H | CN |
| 4-Cl, H | CH$_3$ | H | CN |
| 4-CF$_3$, H | CH$_3$ | H | CN |
| H, H | CH$_3$ | H | CN |

The novel compounds of the general formula (I) are prepared by oxidizing dihydropyridines of the general formula (II)

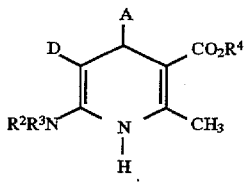

in which

A, D, $R^1$ to $R^3$ have the meaning specified, $R^4$ has the meaning of $R^1$ and $R^{1'}$ specified above, but does not represent hydrogen, in an inert solvent using a typical oxidizing agent, preferably manganese dioxide, optionally alkylating or acylating the products in organic solvents and in the presence of a base and optionally hydrolysing the esters.

The process according to the invention can be illustrated by way of example by the following reaction scheme:

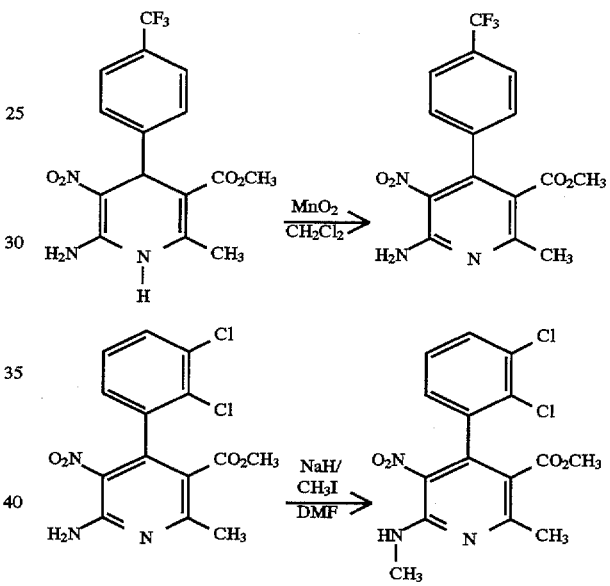

Suitable solvents in this case are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether, acetonitrile, or amides such as hexamethylphosphoramide or dimethylformamide, or acetic acid or halogenated hydrocarbons such as methylene chloride, carbon tetrachloride, or hydrocarbons such as benzene or toluene. It is also possible to use mixtures of the solvents mentioned. Methylene chloride is particularly preferred.

Suitable solvents for the oxidation are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether, acetonitrile, or amides such as hexamethylphosphoramide or dimethylformamide, or acetic acid or halogenated hydrocarbons such as methylene chloride, carbon tetrachloride, or hydrocarbons such as benzene or toluene. It is also possible to use mixtures of the solvents mentioned. Methylene chloride is preferred.

Suitable oxidizing agents in general are 2,3-dichloro-4,5-dicyano-p-benzoquinone and derivatives, pyridinium dichromate, elemental bromine, iodine and manganese dioxide. Manganese dioxide is preferred.

The oxidizing agent is in general employed in an amount from 1 mol to 20 mol, preferably from 1 mol to 5 mol, relative to 1 mol of the compounds of the general formula (II).

The reaction temperatures can be varied within a relatively wide range. In general the reaction is carried out between +10° C. and +150° C., preferably between +20° C. and +100° C., in particular at room temperature.

The reactions can be carried out at normal pressure, but also at elevated or reduced pressure (e.g. 0.5 to 3 bar). In general the reactions are carried out at normal pressure.

Suitable solvents for the alkylation are also customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene or ethyl acetate, or triethylamine, pyridine, dimethyl sulphoxide, dimethylformamide, hexamethylphosphoramide, acetonitrile, acetone or nitromethane. It is also possible to use mixtures of the solvents mentioned. Dimethylformamide is preferred.

Suitable bases are in general alkali metal hydrides or alkoxides, such as, for example, sodium hydride or potassium tert-butoxide, or cyclic amines, such as, for example, piperidine, dimethylaminopyridine or $C_1$–$C_4$-alkylamines, such as, for example, triethylamine. Sodium hydride is preferred.

The reaction temperatures can be varied within a relatively wide range. In general the reaction is carried out between +10° C. and +150° C., preferably between +20° C. and +100° C., in particular at room temperature.

The alkylation is carried out in the abovementioned solvents at temperatures from 0° C. to +150° C., preferably at room temperatures up to +100° C.

The reactions can be carried out at normal pressure, but also at elevated or reduced pressure (e.g. 0.5 to 3 bar). In general the reactions are carried out at normal pressure.

The base is in general employed in an amount from 1 mol to 5 mol, preferably from 1 mol to 2 mol, in each case relative to 1 mol of the compounds to be alkylated.

Suitable bases for the acylation are inorganic or organic bases. These preferably include alkali metal hydroxides such as e.g. sodium hydroxide or potassium hydroxide, alkaline earth metal hydroxides such as e.g. barium hydroxide, alkali metal carbonates such as sodium carbonate or potassium carbonate, alkaline earth metal carbonates such as calcium carbonate, or organic amines (trialkyl($C_1$–$C_6$)amines) such as triethylamine, or heterocycles such as pyridine, methylpiperidine, piperidine or morpholine. Triethylamine is particularly preferred.

Suitable solvents for the acylation are likewise customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoramide, acetonitrile, acetone or nitromethane. It is also possible to use mixtures of the solvents mentioned or also to employ the respective acylating agent as a solvent. Acetic anhydride and pyridine are preferred.

The acylation in general proceeds in a temperature range from 0° C. to +120° C., preferably at +30° C. to +90° C. and at normal pressure.

The hydrolysis of the carboxylic acid esters is carried out according to customary methods by treating the esters in inert solvents with customary bases.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate. Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (e.g. from 0.5 to 5 bar).

Enantiomerically pure forms are obtained e.g. by separating diastereomer mixtures of the compounds of the general formulae (I) and (Ia), in which $R^1/R^{1'}$ represents an optically active ester radical, according to a customary method, then either directly transesterifying or first preparing the chiral carboxylic acids and then preparing the enantiomerically pure compounds by esterification.

The diastereomers are in general separated either by fractional crystallization, by column chromatography or by countercurrent distribution. Which is the optimum process must be decided from case to case; sometimes it is also expedient to use combinations of the individual processes. Separation by crystallization or countercurrent distribution or a combination of both processes is particularly suitable.

The enantiomerically pure compounds are also accessible by chromatography of the racemic esters on chiral phases.

The compounds of the general formula (II) can be prepared, for example, by reacting compounds of the general formula (III)

in which

E and $R^4$ have the meaning specified above, with compounds of the general formula (IV)

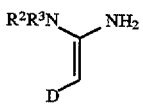

in which

R², R³ and D have the meaning specified above, in one of the abovementioned organic solvents, preferably in ethanol and optionally in the presence of a base.

Suitable bases in general are alkali metal hydrides or alkoxides, such as, for example, sodium hydride or potassium tert-butoxide, or cyclic amines, such as, for example, piperidine, dimethylaminopyridine or $C_1$–$C_4$-alkylamines, such as, for example, triethylamine. Piperidine, dimethylaminopyridine, pyridine, sodium hydride and potassium tert-butoxide are preferred.

The base is in general employed in an amount from 1 mol to 5 mol, preferably from 1 mol to 2 mol, relative to 1 mol of the compounds of the general formula (III).

The reactions can be carried out at normal pressure, but also at elevated or reduced pressure (e.g. 0.5 to 3 bar). In general the reactions arc carried out at normal pressure.

The reaction temperatures can be varied within a relatively wide range. In general, the reaction is carried out between +10° C. and +150° C., preferably between +20° C. and +100° C., in particular at the boiling point of the respective solvent.

The compounds of the general formulae (III) and (IV) are known or can be prepared by customary methods.

$^{86}$Rubidium efflux from C6-BU1 glioma cells

The experiments were carried out with slight changes according to the method described by Tas et al. (Neurosci. Lett. 94, 279–284, (1988)). Rat C6-BU1 glioma cell cultures are used for this. The increase in the efflux above the basal efflux caused by ionomycin is calculated from the data and set as 100%. The stimulations in the presence of test substances are then related to this value.

The present invention also includes pharmaceutical preparations which, in addition to inert, non-toxic, pharmaceutically suitable auxiliaries and excipients, contain one or more compounds of the general formulae (I)/(Ia), or which consist of one or more active compounds of the formulae (I)/(Ia), and processes for the production of these preparations.

The active compounds of the formulae (I)/(Ia) should be present in these preparations in a concentration from 0.1 to 99.5% by weight, preferably from 0.5 to 95% by weight of the total mixture.

In addition to the active compounds of the formulae (I)/(Ia), the pharmaceutical preparations can also contain other pharmaceutical active compounds.

The abovementioned pharmaceutical preparations can be prepared in a customary manner by known methods, for example using the auxiliary(ies) or excipient(s).

In general, it has proven advantageous to administer the active compound(s) of the formulae (I)/(Ia) in total amounts from about 0.01 to about 100 mg/kg, preferably in total amounts from about 1 mg/kg to 50 mg/kg of body weight every 24 hours, if appropriate in the form of several individual doses, to achieve the desired result.

However, it may in some cases be advantageous to depart from the amounts mentioned, mainly depending on the species and on the body weight of the subject treated, on the individual behaviour towards the medicament, the nature and severity of the disorder, the type of preparation and administration, and the time or interval at which administration takes place.

STARTING COMPOUNDS

EXAMPLE I

Methyl 6-amino-4-(3-chloro-4-trifluoromethylphenyl)-1,4-dihydro-2-methyl-5-nitronicotinate

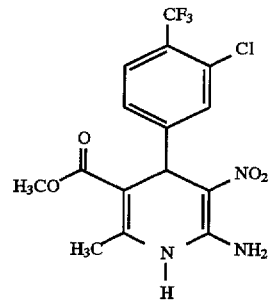

15.3 g (50 mmol) of methyl (3-chloro-4-trifluoromethylbenzylidene)acetoacetate and 5.2 g (50 mmol) of 2-nitro-1,1-ethenediamine (preparation according to R. Troschütz, A. Lückel, Arch. Pharm. (Weinheim) 324, 73–77 (1991)) are dissolved in 80 ml of EtOH and the mixture is kept under reflux for 12 h. After cooling, the resulting solid is filtered off with suction and washed with EtOH. 13.0 g (66% of theory) of the title compound are obtained.

M.p.: 250° C.

EXAMPLE II

Methyl 6-acetylamino-4-(3-chloro-4-trifluoromethylphenyl)-1,4-dihydro-2-methyl-5-nitronicotinoate

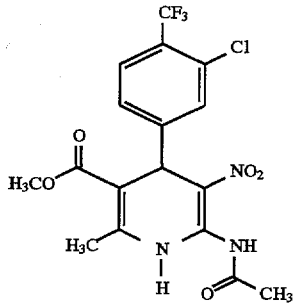

4.0 g (12.0 mmol) of the compound from Example I are dissolved in 40 ml of acetic anhydride and heated under reflux for 12 h. The acetic anhydride is then distilled off under reduced pressure, the residue is dissolved in $CH_2Cl_2$ and the solution is washed with saturated aqueous $NaHCO_3$ solution. The organic phase is dried ($MgSO_4$) and concentrated, and the residue is purified by chromatography on silica gel (toluene/AcOEt/iPrOH 100+10+1). The concentrated eluate is recrystallized from EtOH. 0.5 g (11% of theory) of the title compound is obtained.

M.p.: 152° C.

EXAMPLE III

Methyl 6-amino-5-cyano-2-methyl-4-(trifluoromethylphenyl)-1,4-dihydropyridine-3-carboxylate

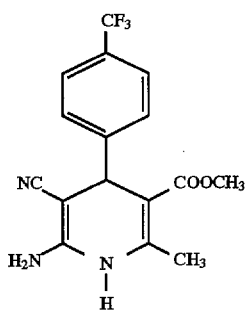

13.6 g (50 mmol) of methyl 2-acetyl-(4-trifluoromethyl) phenylacetate, 7.45 g (50 mmol) of ethyl cyanoacetimidate hydrochloride and 15 g (190 mmol) of ammonium acaate are heated to reflux in 100 ml of MeOH for 1 h. After concentrating, the residue is partitioned between ice water and AcOEt. The organic phase is washed twice with dilute aqueous $NaHCO_3$ solution and once with water, dried over $Na_2CO_3$ and concentrated in vacuo. Crystallization of the residue (18.4 g) from MeOH yields 6.3 g (37% of theory) of colourless crystals.

M.p.: 210°–4° C.

EXAMPLE IV

Methyl 6-acetamido-5-cyano-4-(2,3-dichlorophenyl)-2-methyl-1,4-dihydropyridine-3-carboxylate

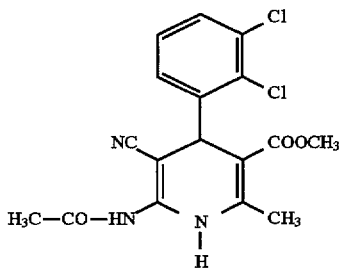

6.7 g (20 mmol) of methyl 6-amino-5-cyano-4-(2,3-dichlorophenyl)-2-methyl-1,4-dihydropyridine-3-carboxylate (preparation analogous to Example III) and 33.5 ml (350 mmol) of acetic anhydride are heated to reflux for 30 min. Excess acetic anhydride is then reacted to give methyl acetate by addition of MeOH with stirring at 25° C. The reaction solution is evaporated in vacuo and stripped off twice with toluene in vacuo. The residue is then boiled with 50 ml of toluene. The deposited crystals are filtered off and washed with toluene.

Yield: 3.6 g (50% of theory)

M.p.: 224° C. (dec.)

EXAMPLE V

Methyl 5-cyano4-(2,3-dichlorophenyl)-2-methyl-6-N-methylamino-1,4-dihydropyridine-3-carboxylate

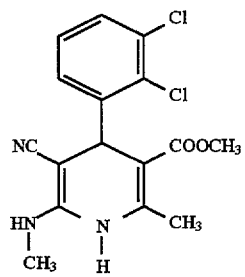

2.8 g (10 mmol) of methyl 2-acetyl-(2,3-dichlorophenyl) acetate and 1.5 g (10 mol) of ethyl cyanoacetimidate hydrochloride are treated with 5 ml of (33% strength) ethanolic methylamine solution (40 mmol). The mixture warms to 46° C. After cooling to 30° C., 2.3 ml (40 mmol) of glacial acetic acid and then 20 ml of MeOH are added. After heating at reflux for 5 h, the reaction solution is treated with ice water and extracted with AcOEt. Drying the organic phase ($Na_2SO_4$) and concentrating it under reduced pressure yields 3.9 g of amorphous residue, which is chromatographed on 100 g of silica gel using toluene/AcOEt (gradient).

Yield: 0.5 g (10% of theory) of crystals

M.p.: 234°–239° C.

PREPARATION EXAMPLES

EXAMPLE 1

Methyl 6-amino-2-methyl-5-nitro4-(4-trifluoromethylphenyl)-nicotinoate

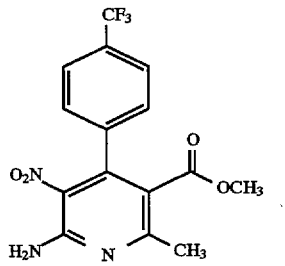

2.0 g (5.6 mmol) of methyl 6-amino-2-methyl-5-nitro-4-(4-trifluoromethyl)-1,4-dihydronicotinoate (preparation analogous to Example I) are dissolved in 100 ml of methylene chloride and treated with 10.0 g of manganese dioxide (precipitated, active). The mixture is stirred at room temperature for 12 h. It is then filtered through silica gel (methylene chloride). The filtrate is concentrated and the residue is recrystallized from methanol. 1.4 g (70% of theory) of the title compound are obtained.

Mp.: 185°–186° C.

The compounds listed in Table 1 are prepared in analogy to the procedure of Example 1:

TABLE 1

| Ex. No. | X | Y | Yield (% of theory) | M.p. °C |
|---|---|---|---|---|
| 2 | H | H | 70 | 202–4 |
| 3 | 3-Cl | 4-CF₃ | 33.5 | 210–2 |
| 4 | 2-Cl | 3-Cl | 70 | 178–9 |
| 5 | 3-NO₂ | H | 96 | 175–77 |
| 6 | 2-CF₃ | H | 41 | 191 |
| 7 | 3-Cl | 4-Cl | 62 | 202–3 |
| 8 | 2-Cl | 3-Cl | 92 | 149–50 (−)-Enant. |
| 9 | 2-Cl | 3-Cl | 90 | 149–50 (+)-Enant. |
| 10 | 4-OCH₃ | H | 25 | 197 |
| 11 | 4-CN | H | 68 | 205–6 |
| 12 | 3-Cl | 2-CN | 5 | 236–9 |

Example 13

Methyl 6-N,N-diacetylamino-2-methyl-5-nitro-4-(2-trifluoromethylphenyl)-nicotinoate

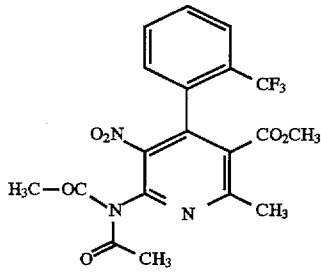

0.8 g (2.25 mmol) of the compound from Example 6 is dissolved in 20 ml of acetic anhydride and heated at reflux overnight. After distilling off the acetic anhydride, the crystalline residue is washed with water and recrystallized from ethanol. 250 mg (28% of theory) of the title compound are obtained.

M.p.: 113° C.

Example 14

Methyl 4-(2,3-dichlorophenyl)-2-methyl-6-N-methylamino-5-nitro-nicotinoate

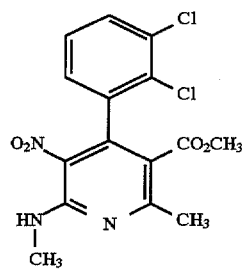

0.7 g (2 mol) of the compound from Example 4 is dissolved in 20 ml of dry DMF and treated with 70 mg of (80% strength) NaH. After stirring at RT for 3 h, the mixture is treated with 2.5 ml of a 1M solution of methyl iodide in DMF and again stirred at room temperature for 18 h. After concentration and filtration through silica gel (AcOEt:toluene 1+10), 0.8 g of crude product is obtained, which is purified by column chromatography (AcOEt:toluene 1+80). 65 mg (9%) are obtained.

The compounds listed in Table 2 are prepared in analogy to the procedure of Example 14:

TABLE 2

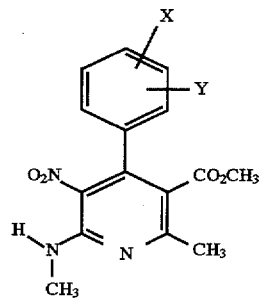

| Ex. No. | X | Y | Yield (% of theory) | M.p. (°C.) |
|---|---|---|---|---|
| 15 | H | H | 20 | 123–4 |
| 16 | 3-Cl | 4-CF₃ | 70 | 148 |
| 17 | 4-CF₃ | H | 56 | 137–8 |
| 18 | 3-NO₂ | H | 23 | 196–7 |
| 19 | 2-CF₃ | H | 20 | 110–1 |

Example 20

Methyl 6-N-acetylamino-4-(2,3-dichlorophenyl)-2-methyl-5-nitronicotinoate

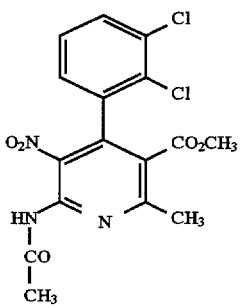

800 mg (2 mmol) of methyl 6-N-acetylamino-4-(2,3-dichlorophenyl)-1,4-dihydro-2-methyl-5-nitronicotinoate (prepration analogous to Example II) are dissolved in 80 ml of methylene chloride and treated with 5 g of $MnO_2$. The mixture is stirred at room temperature for 3 d. After filtration through Celite and column chromatography (AcOEt:toluene 4+1), the concentrated eluate is recrystallized from toluene. 302 mg (38% of theory) of the title compound are obtained.

M.p.: 195° C.

The compounds listed in Table 3 are prepared in analogy to the procedure of Example 20:

TABLE 3

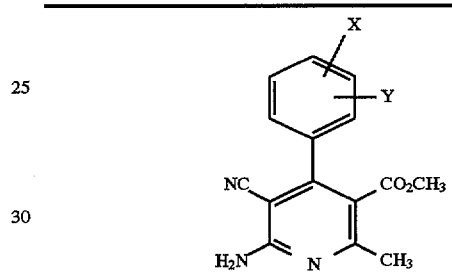

| Ex. No. | X | Y | Yield (% of theory) | M.p. °C. |
|---|---|---|---|---|
| 21 | H | H | 19 | 178–9 |
| 22 | 2-CF₃ | H | 64 | 141–2 |

Example 23

Methyl 6-amino-5-cyano-4-(2,3-dichlorophenyl)-2-methylnicotinoate

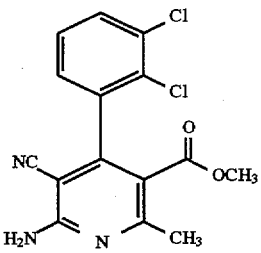

1.0 g (3 mmol) of methyl 6-amino-5-cyano-4-(2,3-dichlorophenyl)-2-methyl-1,4-dihydronicotinoate (preparation analogous to Example III) and 2.6 g (30 mmol) of manganese dioxide are stirred in 20 ml of methylene chloride at room temperature for 70 h. The solvent is stripped off in vacuo and the residue is treated with ethyl acetate and filtered through silica gel. 0.6 g (60% of theory) of the title compound is obtained (colourless crystals).

M.p.: 251°–253° C.

Example 24

Methyl 6-amino-5-cyano-4-(3-nitrophenyl)-2-methylnicotinoate

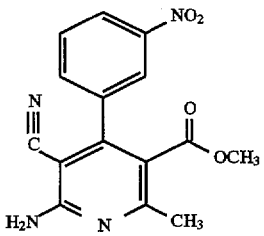

The title compound is prepared in analogy to the procedure of Example 20.

$R_f$: 0.19 (tol: $AcOC_2H_5$ 3:1)

M.p.°C.: 202–5

Yield: 80% of theory

The compounds listed in Table 4 are prepared in analogy to the procedure of Examples 23 and 24:

TABLE 4

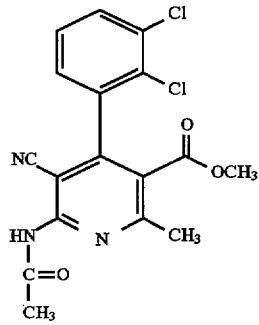

| Ex. No. | X, Y | Yield (% of theory) | M.p. (°C.) |
|---|---|---|---|
| 25 | H, H | 55 | 254–8 |
| 26 | 2-CF₃, H | 45 | 212 |
| 27 | 2-Cl, H | 65 | 231 |
| 28 | 2-CF₃, H | 85 | 201–5 |
| 29 | 4-C₆H₅, H | 38 | 241–4 |

Example 30

Methyl 6-acetamido-5-cyano-4-(2,3-dichlorophenyl)-2-methyl-1,4-dihydropyridine-3-carboxylate Analogously to the preparation procedure of Example 23, 4.3 g (11 mmol) of the compound from Example IV are reacted to give 1.4 g (34% of theory) of the title compound by oxidation with 10.7 g (120 mmol) of manganese dioxide.

Mp.: 160°–2° C. (ethyl acetate).

The compounds listed in Table 5 are prepared in analogy to the procedure of Example 30:

TABLE 5

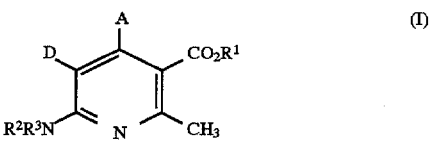

| Ex. No. | X, Y | Yield (% of theory) | M.p. (°C.) |
|---|---|---|---|
| 31 | 3-NO$_2$, H | 11 | 189–92 |
| 32 | 2-CF$_3$, H | 32 | 180–3 |
| 33 | 4-CF$_3$, H | 52 | 139–42 |

Methyl 5-cyano-4-(2,3-dichlorophenyl)-2-methyl-6-N-methylaminopyridine-3-carboxylate

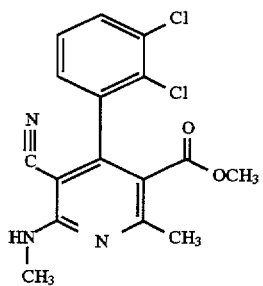

In analogy to the procedure of Example 20, 3.5 g (10 mmol) of the compound from Example V are reacted to give 1.7 g (49% of theory) of the title compound by oxidation with 10 g (115 mmol) of manganese dioxide.

The compounds listed in Table 6 are prepared in analogy to the procedure of Example 34:

TABLE 6

| Ex. No. | X, Y | Yield (% of theory) | M.p. (°C.) |
|---|---|---|---|
| 35 | 3-NO$_2$, H | 10 | 213–4 |
| 36 | 2-CF$_3$, H | 64 | 128–31 |
| 37 | 4-Cl, H | 40 | 152–4 |
| 38 | 4-CF$_3$, H | 30 | 175–9 |
| 39 | H, H | 70 | 121–4 |

We claim:

1. A method of treating diseases which are affected by modulating the calcium-dependent potassium channel which comprises administering to a patient in need thereof an effective amount of a 4-phenyl-6-amino-dihydropyridine of the formula $$\text{(I)}$$

in which

A represents aryl having 6 to 10 carbon atoms or pyridyl, each of which is optionally substituted up to 3 times by identical or different substituents selected from the group consisting of nitro, cyano, phenyl, halogen and trifluoromethyl or by straight-chain or branched alkylthio or alkoxy in each case having up to 6 carbon atoms, D represents cyano or nitro, $R^1$ represents hydrogen or straight-chain or branched alkyl having up to 8 carbon atoms, $R^2$ and $R^3$ are identical or different and represent hydrogen or straight-chain or branched alkyl or acyl in each case having up to 6 carbon atoms, or a salt thereof.

2. The method according to claim 1, wherein

A represents phenyl or naphthyl, each of which is optionally substituted up to 3 times by identical or different substituents selected from the group consisting of nitro, cyano, fluorine, chlorine, bromine, iodine, phenyl and trifluoromethyl or by straight-chain or branched alkylthio or alkoxy in each case having up to 4 carbon atoms, D represents cyano or nitro, $R^1$ represents hydrogen or straight-chain or branched alkyl having up to 6 carbon atoms, $R^2$ and $R^3$ are identical or different and represent hydrogen or straight-chain or branched alkyl or acyl in each case having up to 4 carbon atoms, or a salt thereof.

3. The method according to claim 1, wherein

A represents phenyl which is optionally substituted up to 2 times by identical or different substituents selected from the group consisting of nitro, cyano, fluorine, chlorine, bromine, iodine, phenyl, trifluoromethyl, methoxy and methylthio, D represents cyano or nitro, $R^1$ represents hydrogen or straight-chain or branched alkyl having up to 4 carbon atoms, $R^2$ and $R^3$ are identical or different and represent hydrogen or straight-chain or branched alkyl or acyl in each case having up to 3 carbon atoms, or a salt thereof.

4. The method according to claim 1, wherein the disease is a disease of the CNS.

5. The method according to claim 1, wherein the disease is a cerebral disease.

6. The method according to claim 1, wherein the disease is a disease associated with brain function disorders in old age, organic brain syndrome or age-associated with memory impairment.

7. The method according to claim 1, wherein the disease is a cerebral ischaemia, stroke, craniocerebral traumata, or subarachnoid haemorrhages.

8. The method according to claim 1, wherein the disease is depression or a psychosis.

9. The method according to claim 1, wherein the disease is a disorder of the immune system.

10. A 4-phenyl-6-amino-nicotinic acid compound of the formula

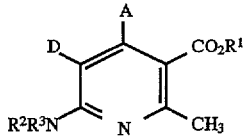

(I)

in which

A represents aryl having 6 to 10 carbon atoms or pyridyl, each of which is optionally substituted up to 3 times by identical or different substituents selected from the group consisting of nitro, cyano, phenyl, halogen and trifluoromethyl or by straight-chain or branched alkylthio or alkoxy in each case having up to 6 carbon atoms, D represents cyano or nitro, $R^1$ represents hydrogen or straight-chain or branched alkyl having up to 8 carbon atoms, $R^2$ and $R^3$ are identical or different and represent hydrogen or straight-chain or branched alkyl or acyl in each case having up to 6 carbon atoms or a salt thereof, where ethyl 6-amino-5-cyano-2-methyl-4-phenyl-nicotinate, ethyl 6-amino-4-(4-chlorophenyl)-5-cyano-2-methyl-nicotinoate, ethyl 6-amino-5-cyano-2-methyl-4-(4-methoxyphenyl)-nicotinoate and ethyl 6-amino-5-cyano-2-methyl-4-(4-nitrophenyl)-nicotinoate are excluded.

11. A pharmaceutical composition which comprises an effective amount of a compound according to claim 10 and a pharmaceutically acceptable auxiliary or excipient.

12. A process for the preparation of a 4-phenyl-6-amino-nicotinic acid compound according to claim 10 which comprises oxidizing a dihydropyridine of the formula

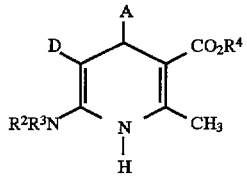

(II)

in which

A, D, $R^1$ to $R^3$ have the specified meaning in claim 10 and $R^4$ represents straight-chain or branched alkyl having up to 8 carbon atoms, in an inert solvent and in the presence of an oxidizing agent.

13. The process according to claim 12, wherein the oxidizing agent is manganese dioxide.

* * * * *

UNITED STATES PATENT AND TRADEMARK OFFICE
CERTIFICATE OF CORRECTION

PATENT NO. : 5,670,525
DATED : September 23, 1997
INVENTOR(S) : Urbahns, et al.

It is certified that error appears in the above-indentified patent and that said Letters Patent is hereby corrected as shown below:

Col. 17, next to last line     Delete " nicotinate " and substitute -- nicotinoate --

Signed and Sealed this

Twenty-eighth Day of April, 1998

Attest:

BRUCE LEHMAN

*Attesting Officer*     *Commissioner of Patents and Trademarks*